US006984525B2

(12) United States Patent
Minarik

(10) Patent No.: US 6,984,525 B2
(45) Date of Patent: Jan. 10, 2006

(54) METHOD FOR AUTOMATED ISOLATION OF FRACTIONS IN MULTICHANNEL SEPARATION SYSTEMS

(75) Inventor: Milan Minarik, Orech (CZ)

(73) Assignee: Watrex Praha, s.r.o., Prague (CZ)

( * ) Notice: Subject to any disclaimer, the term of this patent is extended or adjusted under 35 U.S.C. 154(b) by 524 days.

(21) Appl. No.: 10/196,782

(22) Filed: Jul. 16, 2002

(65) Prior Publication Data
US 2003/0015424 A1 Jan. 23, 2003

Related U.S. Application Data

(60) Provisional application No. 60/305,960, filed on Jul. 18, 2001.

(51) Int. Cl.
*G01N 30/80* (2006.01)
*G01N 30/82* (2006.01)

(52) U.S. Cl. .................. 436/164; 436/161; 436/172; 436/177; 436/178; 422/70; 422/82.05; 422/82.08; 422/82.09; 422/101; 73/61.58; 204/451; 204/452; 204/455; 204/457; 204/601; 204/602; 204/603; 204/607; 210/198.2; 210/656; 356/344

(58) Field of Classification Search ................ 436/161, 436/164, 172, 177, 178; 422/70, 99, 101, 422/82.05, 82.08, 82.09; 204/451, 452, 455, 204/457, 601, 602, 603, 607; 210/198.2, 210/656; 73/61.58; 356/344
See application file for complete search history.

(56) References Cited

U.S. PATENT DOCUMENTS 5,541,420 A * 7/1996 Kambara .................... 204/602
6,387,235 B1 * 5/2002 Irie et al. ................... 204/601
6,660,149 B1 * 12/2003 Karger et al. ............... 204/601

OTHER PUBLICATIONS

O. Muller et al., "Design of a High-Precision Fraction Collector for Capillary Electrophoresis", Anal. Chem., 1995, vol. 67, pp. 2974-2980.
M. Minarik et al., "Design of a Fraction Collector for Capillary Array Electrophoresis", Electrophoresis 2002, vol. 23, pp. 35-42.
T. Irie et al., "Automated DNA Fragment Collection by Capillary Array Gel Electrophoresis in Search of Differentially Expressed Genes", Electrophoresis 2000, vol. 21, pp. 367-374.

* cited by examiner

*Primary Examiner*—Jan M. Ludlow
(74) *Attorney, Agent, or Firm*—Schneck & Schneck; Thomas Schneck; David M. Schneck

(57) ABSTRACT

A method to collect a plurality of target zones from a plurality of channels. The method includes introducing a plurality of compound mixtures into a plurality of microchannels on a microfabricated chip or a capillary tube. Optical signal measured at a detector window provides a signal of the position of a target zone. When a target zone has migrated to the location of a detector window, the detector senses an optical signal from the target zone and signals the system to disconnect a driving force from that channel. Once a plurality of zones in a plurality of channels are aligned, the driving force is reconnected and the zones are coeluted into a collection container.

8 Claims, 2 Drawing Sheets detector

METHOD FOR AUTOMATED ISOLATION OF FRACTIONS IN MULTICHANNEL SEPARATION SYSTEMS

CROSS-REFERENCE TO RELATED APPLICATION

This application claims priority from U.S. provisional application No. 60/305,960, filed Jul. 18, 2001.

TECHNICAL FIELD

The present invention relates generally to separation and analysis of compounds and more specifically to means of isolating compounds separated by techniques employing a plurality of separation channels.

BACKGROUND OF THE INVENTION

Current advances in research of biological compounds require sensitive techniques for their separation and analysis. Many of these techniques are based on sample isolation from crude mixtures followed by their further processing, analysis and identification. The separation can be achieved by electromigration in an electric field (electrophoresis), by partitioning between mobile and stationary phases (chromatography) or by combination of the two (electrochromatography). The initial separation can be followed by isolation of separated fractions and their further processing by undergoing various chemical or enzymatic reactions. The resulting products are then visualized and identified by UV or fluorescence signals, mass spectra or NMR spectra and other detection methods.

Many current separation techniques exhibit high resolution and small sample consumption, resulting from miniaturization of separation compartments. Electrophoresis and chromatography is often carried out in narrow-bore columns, fused silica capillaries or miniaturized channels fabricated on silicon chips. In order to isolate the separated compounds, various microscale fraction collection techniques were introduced (See Muller, O; Foret, F.; Karger, B. L.; Design of a high precision fraction collector for capillary electrophoresis. Analytical Chemistry (1995) v. 67, p. 2974–80). The most straightforward technique relies on elution of separated zones into individual collection vessels replaced at the channel exit at time intervals calculated from migration velocity. The more advanced collection devices include sheath flow or moving belt interfaces enabling a semi-continuous operation without a need to interrupt the separation when replacing the collection vessels.

The above mentioned fraction collection techniques are applicable to single channel systems. In order to increase throughput of sample processing, many separations are carried out in a parallel fashion using multiple separation channels. Most common multiplexed separation systems consist of arrays of narrow-bore fused silica capillaries or microfabricated arrays of channels on silicon chips. Currently, there are no commercially available multichannel instruments equipped with an option of isolation and/or fraction collection. The main problem that hinders multichannel collection is the timing, since zones usually elute from different channels at different times. Multichannel collector utilizing multiple individually controlled collection tracks has been proposed (See Irie, T., et al. Automated DNA fragment collection by capillary array gel electrophoresis in search of differentially expressed genes. Electrophoresis (2000) v. 21, p. 367–374) but this approach requires a very complex instrumentation. In addition, only cross-linked separation matrices can be used, to resist laminar flow induced in each separation capillary by the collection sheath flow. An alternative design was demonstrated using a "comprehensive collection" in which zones are collected in predefined time intervals regardless of the actual zone starts and ends. (See Minarik, M.; et al., Design of a fraction collector for capillary electrophoresis. Electrophoresis (2002) v. 23, p. 35–42.) This approach is very effective, however, the total number of capillaries is limited (typically 12 to 16) due to the requirement of capillaries forming a single row cone. This limitation disallows its direct application to currently existing multicapillary instruments (e.g. 8-, 16- or 96-capillary), where capillaries are arranged in a 2-dimensional fashion with rows and columns.

It is an object of the invention to provide means of collecting individual samples from multiple separation channels.

It is a further object of the invention to provide a method allowing collection of compounds from independent channels using a collection device with a simple control.

It is a further object to provide method applicable to available multi-channel separation instruments without a need of complex changes in instrumentation design.

SUMMARY OF THE INVENTION

The above objects have been achieved through the alignment of zones detected in different separation channels at a fixed position close to the channel ends by selectively disconnecting a driving force (e.g. voltage, a hydrodynamic pressure, a combination of the two, or another separating force) in individual channels after a target zone has reached a detector window, followed by parallel elution of all pre-aligned zones into a single collection microtiter plate when re-applying a driving force to all channels. The main area of applicability is in high-throughput analysis including analysis of protein mixtures, identification of protein structure, DNA separations, gene expression and discovery, detection and screening of genetic variations.

BRIEF DESCRIPTION OF THE DRAWINGS

FIG. 1B is a graph of detected optical signal at a detection window of the capillaries in FIG. 1A.

FIG. 2B is a graph of detected optical signal at a detection window of the capillaries in FIG. 2A

FIG. 3B is a graph of detected optical signal at a detection window of the capillaries in FIG. 3A.

DETAILED DESCRIPTION OF THE INVENTION

Figure 1A:
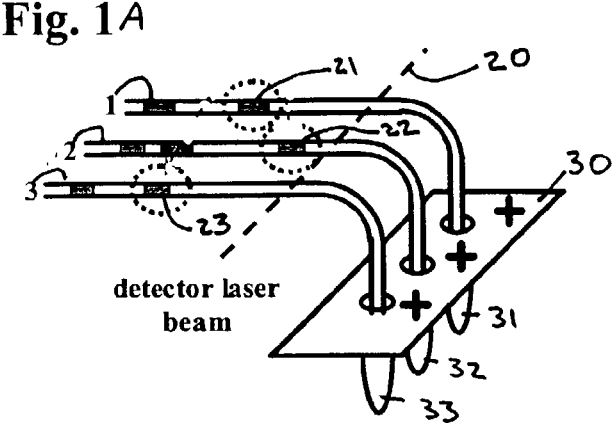
FIG. 1A is a perspective view of non-uniform migration in three capillary tubes.
Figure 1A:
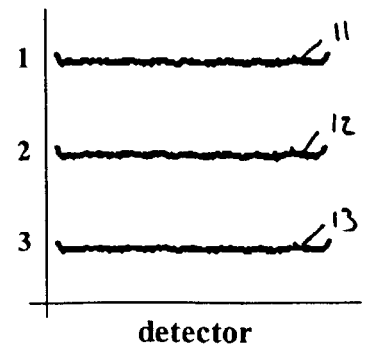
Figure 2A:
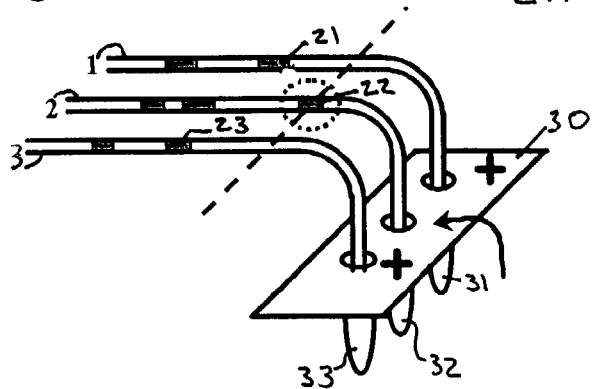
FIG. 2A is a perspective view of non-uniform migration in three capillary tubes at a time when a zone in the first capillary reaches a detector window.
Figure 2A:
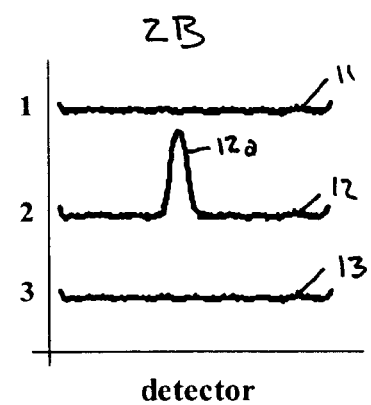
Figure 3A:
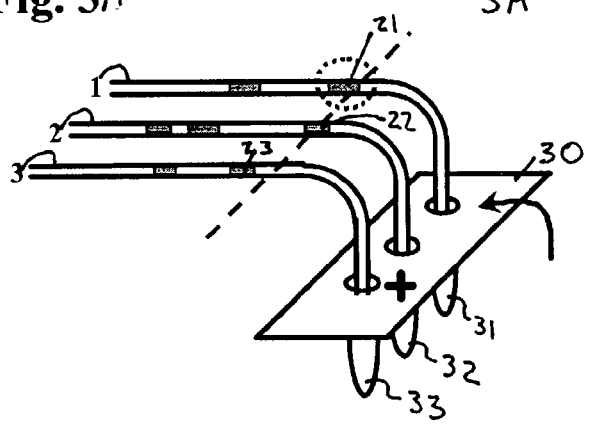
FIG. 3A is a perspective view of non-uniform migration in three capillary tubes at a time when a second zone reaches the detector window.
Figure 3A:
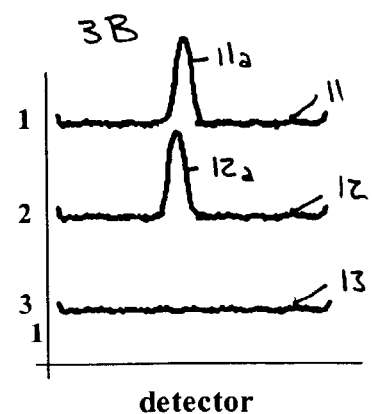

In the described method a new approach to fraction collection from array of multiple channels is presented. In one embodiment it utilizes elution and collection into standard microtiter plates. In multichannel system zones may initially not be aligned during a separation (as shown in FIG. 1A). As a result zones elute from different channels at different times. In order to collect compounds from different channels 1, 2, 3 into a single collection vessel 30 having compartments 31, 32, 33, desired zones 21, 22, 23 have to be first aligned at the same position. This can be done by disconnecting the driving force in individual channels (e.g. disconnecting voltage in case of electrophoresis). After a zone to be collected in particular channel is detected as the zone migrates to a detector window. The detector readout is shown in FIGS. 1B–4B. In FIG. 1B the graph shows no detection at the detection windows of capillaries 1, 2, or 3.

With reference to FIGS. 1–4A and 5 a laser beam 20 is illuminating a detection window on capillaries 1, 2, 3. If the target zones 21, 22, 23 are optically labeled (e.g. with a fluorescent dye) such that when laser beam 20 illuminates the targeted zones 21, 22, 23 an optical signal may be measured by a detector. After the voltage in channel 2 is disconnected (as indicated by the arrow), corresponding zone 22 is stationary at the location of the detector window, as shown in FIG. 2A. By repeating this procedure (i.e. separation in each channel until the target zone reaches a detector window), desired fractions from all channels are consequently aligned in the detector window or in any arbitrary position behind the window as shown schematically for two channels in FIG. 3A (in which migration of a second zone 21 is stopped by disconnecting a driving force) and 4 (in which migration of the third zone 23 is stopped). In FIGS. 1–4A, and 5, connection of the driving force is indicated by a "+". In FIGS. 2–4A, the arrows indicate the capillary in which the driving force is turned off, stopping migration of the target zone.

Figure 4A:
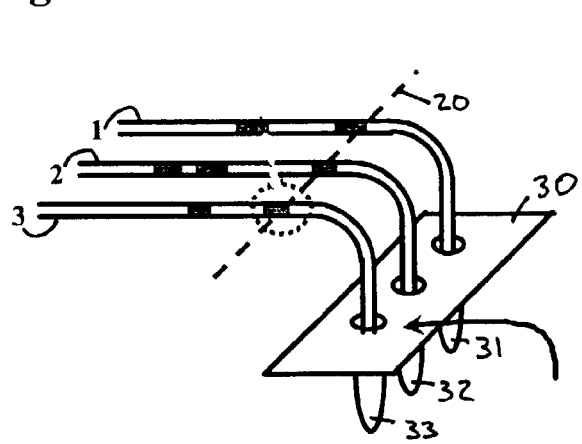
FIG. 4A is a perspective view of non-uniform migration in three capillary tubes at time when a third zone reaches a detection window.
Figure 4B:
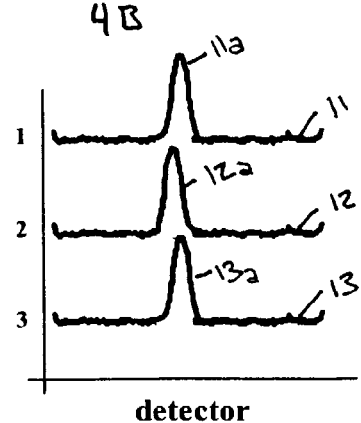
FIG. 4B is a graph of the detected optical signal at a detection window of the capillaries in FIG. 4A.

In FIGS. 1–4B, the graphs showing a detector reading from each of the three capillaries is shown. Lines 11, 12, and 13 show the detector reading from capillaries 1, 2, 3 respectively. In FIG. 1B, lines 11, 12, and 13 are flat, indicating no detection of the target zones in the detection window. In FIG. 2B line 12 contains a peak 12a, indicating that a target zone is at the detector window. In the driving force is turned off, this signal will continue to be detected, as shown in FIGS. 3B, 4B. In FIG. 3B lines 11 and 12 have peaks 11a and 12a, indicating that the targeted zones are at the detection window location in respective capillaries 1, 2. The driving force is then turned off in capillaries 1, and 2. FIG. 4B shows lines 11, 12, and 13 have peaks 11a, 12a, and 13a indicating that the target zone is in the detection window in all three capillaries. At this time the driving force could be restored to all capillaries and the zones eluted together.

Figure 5:
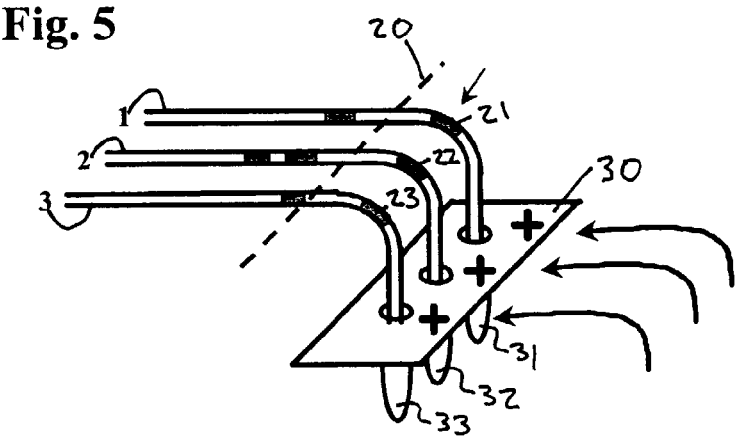
FIG. 5 is a perspective view of three capillaries in which zones previously aligned in detection position are co-eluted into a set of collection vials.

In order to prevent band spreading due to diffusion of the waiting bands, the waiting interval should be limited depending on the level of band dispersion (usually several minutes per each array of fractions). Subsequently zones migrating past the detector window after the interval during which target zones have been aligned will be collected in the next collection interval. Thus sequences of alignment and migration allow collection of a number of different target zones from each channel separation. At the end of each collection interval, the new (collection) well plate is positioned at the channel exit and the voltage is reconnected (as indicted in the arrows in FIG. 5) in all channels to elute all fractions simultaneously. Considering the short distance remaining between the detector window and the end of the channels, the time needed to reach the end is approximately same for zones 21, 22, 23 in all channels 1, 2, 3, which can then all be collected in parallel into a single microtiter plate 30 as shown in FIG. 5.

What is claimed is:

1. A method for isolation and fraction collection of compounds from a plurality of separation channels in a multiplexed separation system, the method comprising:
    a) introducing compound mixtures into said plurality of separation channels;
    b) applying a driving force to each separation channel such that zones migrate through each separation channel;
    c) continuously detecting at a detector window an optical signal from each separation channel;
    d) disconnecting said driving force individually in each individual separation channel once a targeted zone has been detected in said individual separation channel;
    e) reconnecting said driving force once said targeted zones in said plurality of separation channels are aligned, as indicated by detection of said optical signal from said targeted zones, said optical signal emitted at said detector window in each separation channel; and
    f) eluting said targeted zones.

2. The method of claim 1, wherein said plurality of separation channels each extend through a fused silica capillary.

3. The method of claim 1, wherein said plurality of separation channels each are a part of a microfabricated chip.

4. The method of claim 1, wherein said driving force is an electric field.

5. The method of claim 1, wherein said driving force is hydrodynamic pressure.

6. The method of claim 1, wherein said driving force is a combination of an electrical field and hydrodynamic pressure.

7. The method of claim 1, wherein said targeted zones are detected by UV absorbance.

8. The method of claim 1, wherein said targeted zones are detected by fluorescence detection.

* * * * *

UNITED STATES PATENT AND TRADEMARK OFFICE
CERTIFICATE OF CORRECTION

PATENT NO. : 6,984,525 B2 Page 1 of 1
APPLICATION NO. : 10/196782
DATED : January 10, 2006
INVENTOR(S) : Milan Minarik It is certified that error appears in the above-identified patent and that said Letters Patent is hereby corrected as shown below:

Column 3, line 20, "With reference to FIGS. 1-4A and 5 a laser ..." should read:
--With reference to FIGS. 1A-4A and 5A a laser --.

Column 3, line 36 "...In FIGS. 1-4A, and 5, connection of the driving ..." should read: --In FIGS. 1A-4A, and 5A, connection of the driving…--.

Column 3, line 37, "...In FIGS. 2-4A, the arrows indicate ..." should read:
--In FIGS. 2A-4A, the arrows indicate --.

Column 3, line 40, "In FIGS. 1-4B, the graphs showing a detector..." should read:
--In FIGS. 1B-4B, the graphs showing a detector--.

Signed and Sealed this

Second Day of January, 2007

JON W. DUDAS
*Director of the United States Patent and Trademark Office*